Dec. 9, 1958 W. KORDES Plant Pat. 1,778
ROSE PLANT
Filed April 3, 1958
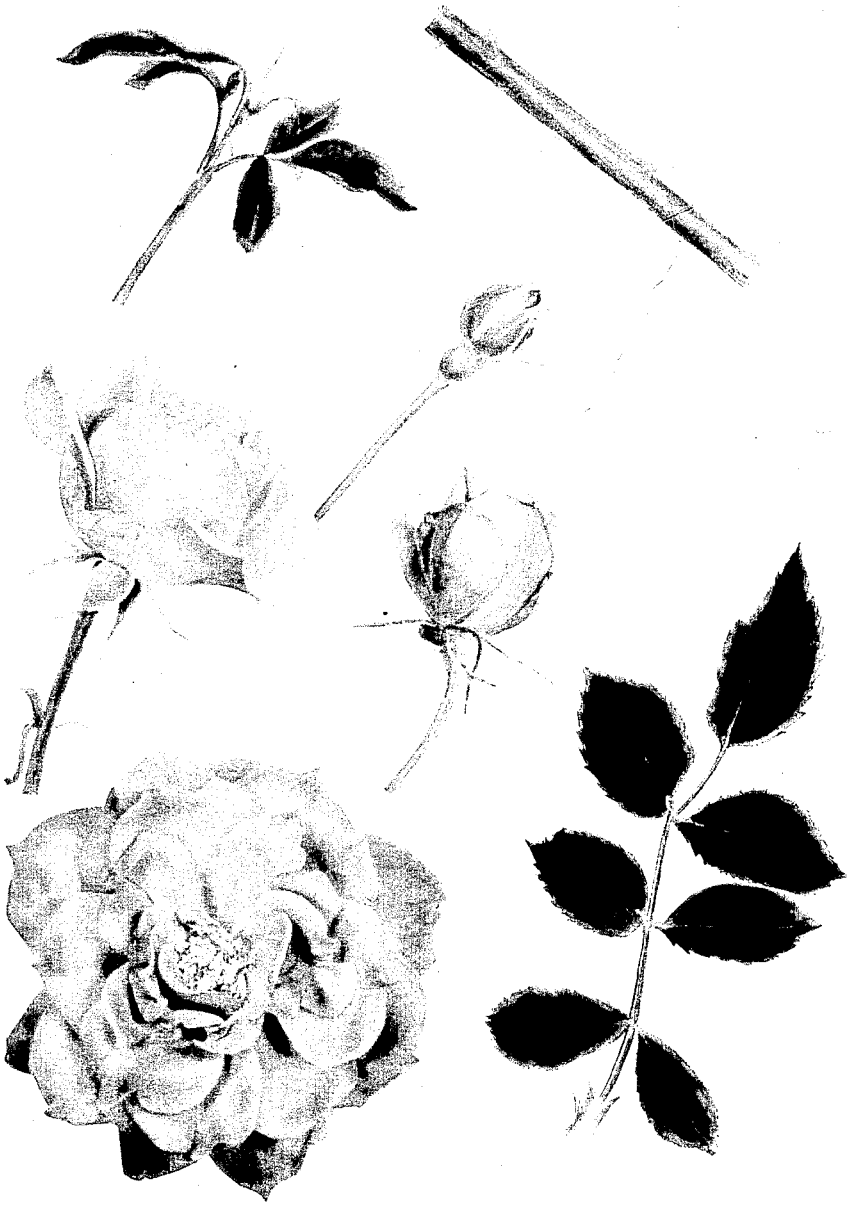
Inventor
Wilhelm Kordes
By: Robert Cobb
Attorneys.

United States Patent Office

Plant Pat. 1,778
Patented Dec. 9, 1958

1,778

ROSE PLANT

Wilhelm Kordes, near Elmshorn in Holstein, Sparrieshoop, Germany, assignor to Jackson & Perkins Company, Newark, N. Y., a corporation of New York Application April 3, 1958, Serial No. 726,301

1 Claim. (Cl. 47—61)

The present invention relates to a new and distinct variety of rose plant of the large-flowered polyantha class, which was originated by me by crossing the variety "Rudolph Timm" (unpatented) with the variety known in Germany as "Kordes' Sondermeldung," but known in the U. S. as "Independence" (U. S. Plant Patent No. 1,036).

The primary objective of this breeding was to produce a new rose variety which bears flowers corresponding in color to those of the variety "Independence," but which is endowed with more vigorous and unright habits of growth such as characterize the variety "Rudolph Timm." This objective was fully achieved, along with other improvements, as evidenced by the following unique combination of characteristics which are outstanding in the new variety and distinguish it from its parents, as well as from all other varieties of which I am aware:

(1) Vigorous and upright habits of growth;
(2) Free-flowering habit;
(3) Bright-colored thorns;
(4) High-colored (Oxblood Red) young shoots;
(5) Scarlet Red, lightly overcast with Scarlet general color tonality of the flowers, which constitutes an attractive and highly colored flower; and
(6) Eminent suitability for use in greenhouse pot forcing.

Asexual reproduction of the new variety by budding, as performed at Newark, New York, U. S. A. and also at Pleasanton, California, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Rudolph Timm."
*Pollen parent.*—"Independence."
Classification:
*Botanic.*—Large-flowered polyantha.
*Commercial.*—Floribunda.

*Flower*

(Observations made from specimens grown in a greenhouse at Newark, New York, U. S. A., near mid-morning in the latter part of April.)

Blooming habit: Recurrent—continuous.
Bud:
*Size.*—Medium.
*Form.*—Ovoid; is not affected by wet or hot weather.
*Color.*—When sepals first divide—Pomegranate Purple, Plate 12. When petals begin to unfurl—Scarlet Red, Plate 1, lightly overcast in the lower half of the petal with Nopal Red, Plate 1. When half-blown: inside of petals—Scarlet Red, Plate 1, lightly overcast with Scarlet, Plate 1; reverse of petals—Scarlet Red, Plate 1.

*Sepals.*—Slightly branched; curl back when petals begin to unfurl. Color: inside—Turtle Green, Plate 32; outside—Light Bice Green, Plate 17.
*Calyx.*—Color—Light Bice Green, Plate 17. Shape—pear. Size—small. Aspect—smooth. Odor when rubbed—none.
*Peduncle.*—Length — medium. Aspect — smooth. Strength—erect; slender. Color—Spinach Green, Plate 5.
*Opening.*—Opens up well; is not affected by adverse weather conditions.
Bloom:
*Size.*—Medium. Average size when fully expanded—3 inches.
*Borne.*—Both singly and several together.
*Stems.*—Medium length; strong.
*Form (when first open).*—Cupped. Permanence—retains its form to the end, but outer petals curl back.
*Petalage.*—Double (full but open center). Number of petals under normal conditions—from 25 to 30.
*Color.*—Center of flower—Scarlet, Plate 1, lightly overcast with Scarlet Red, Plate 1. Outer petals—Scarlet Red, Plate 1. Base of petals (aiglet)—Spinel Pink, Plate 26. Inside of petals—Scarlet Red, Plate 1, lightly overcast with Scarlet, Plate 1. Reverse of petals—Spectrum Red, Plate 1, lightly overcast with Scarlet, Plate 1. General tonality from a distance—Scarlet Red, Plate 1.
*Discoloration.*—General tonality at end of first day—Scarlet Red, Plate 1. Second day—Scarlet Red, Plate 1, lightly overcast with Scarlet, Plate 1. Third day—Scarlet Red, Plate 1, lightly overcast with Scarlet, Plate 1.
Petals:
*Texture.*—Thick; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Deep Chrome, Plate 3.
Stamens, filaments (threads): Medium length. Color—Sulphur Yellow, Plate 5.
Pollen: Color—Pale Yellow-Orange, Plate 3.
Styles: Loosely separated; medium length; thin.
Stigmas: Color—Maize Yellow, Plate 4.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Abundant.
*Color.*—New foliage: upper side—Oxblood Red, Plate 1; under side—Oxblood Red, Plate 1, lightly overcast with Van Dyke Red, Plate 13. Old foliage: upper side—Cerro Green, Plate 5; under side—Light Elm Green, Plate 17.

*Shape.*—Oval.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Rainette Green, Plate 31. Under side—smooth.

*Stipules.*—Medium length; smooth.

Wood:

*New wood.*—Color—Van Dyke Red, Plate 13. Bark—smooth.

*Old wood.*—Color—Light Elm Green, Plate 17. Bark—smooth.

Thorns:

*Thorns.*—Quantity: on main stalks from base—ordinary; on laterals from stalk—ordinary. Form—narrow base; medium length; straight. Color (when young)—Old Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of vigorous and upright habits of growth, free-flowering habit, bright-colored thorns, high-colored young shoots, high-colored flowers corresponding to Scarlet Red, lightly overcast with Scarlet in general color tonality, and eminent suitability for greenhouse pot forcing use.

No references cited.